United States Patent
Becicka

(10) Patent No.: US 8,039,621 B2
(45) Date of Patent: Oct. 18, 2011

(54) PROCESS FOR PREPARING ANHYDROUS ARIPIRAZOLE TYPE I

(75) Inventor: Brian T. Becicka, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 223 days.

(21) Appl. No.: 12/445,771

(22) PCT Filed: Oct. 24, 2007

(86) PCT No.: PCT/US2007/022483
§ 371 (c)(1),
(2), (4) Date: Apr. 16, 2009

(87) PCT Pub. No.: WO2008/051541
PCT Pub. Date: May 2, 2008

(65) Prior Publication Data
US 2010/0317857 A1    Dec. 16, 2010

Related U.S. Application Data

(60) Provisional application No. 60/853,768, filed on Oct. 24, 2006.

(51) Int. Cl.
*C07D 215/227* (2006.01)
(52) U.S. Cl. .................... 544/363; 514/253.07
(58) Field of Classification Search .................... None
See application file for complete search history.

(56) References Cited

U.S. PATENT DOCUMENTS

| | | |
|---|---|---|
| 4,734,416 A | 3/1988 | Banno et al. |
| 4,824,840 A | 4/1989 | Banno et al. |
| 5,006,528 A | 4/1991 | Oshiro et al. |
| 2004/0058935 A1 | 3/2004 | Bando et al. |
| 2005/0152981 A1 | 7/2005 | Gleeson et al. |
| 2005/0277650 A1 | 12/2005 | Venkataraman et al. |
| 2006/0142579 A1 | 6/2006 | Ettema et al. |
| 2009/0247542 A1* | 10/2009 | Benito Velez et al. ... 514/253.07 |

FOREIGN PATENT DOCUMENTS

| | | |
|---|---|---|
| CA | 2379005 A1 | 3/2003 |
| EP | 1419776 A3 | 6/2004 |
| WO | 03026659 A1 | 4/2003 |
| WO | 2005058835 A2 | 6/2005 |
| WO | 2006012237 | 2/2006 |
| WO | 2007004061 | 1/2011 |

OTHER PUBLICATIONS

International Search Report, Apr. 22, 2008.
Satoshi Aoki et al., "Study on Crystal Transformation of Aripiprazol" CR.119, The Fourth Japan-Korea Symposium on Separation Technology, Oct. 6-8, 1996, Waseda University International Conference Center, Tokyo, Japan. pp. 937-940.
Anderson et al., "Tools for purifying the product: column chromatography, crystallizaton and reslurrying," Practical Process Research and Development, p. 223-247, Jan. 1, 2000.
Supplementary European Search Report dated Mar. 2, 2011 in European Application No. 07852898.(8 pages).

* cited by examiner

*Primary Examiner* — Emily Bernhardt
(74) *Attorney, Agent, or Firm* — Banner & Witcoff, Ltd.

(57) ABSTRACT

Type I anhydrous aripiprazole is prepared by dissolving aripiprazole (or an acid salt thereof) in an alcoholic solvent, optionally containing water, at elevated temperature, adding seed crystals of Type 1 anhydrous aripiprazole to the solution, cooling the mixture, and isolating crystals aripiprazole and drying the isolated crystals to obtain low moisture Type 1 anhydrous aripiprazole.

9 Claims, 6 Drawing Sheets

PROCESS FOR PREPARING ANHYDROUS ARIPIRAZOLE TYPE I

FIELD OF THE INVENTION

The present invention relates to an improved process for the preparation of anhydrous 7-[4-[4-(2,3-dichlorophenyl)-1-piperazinyl]butoxy]-3,4-dihydro-2-(1H)-quinolinone (Type I) (Anhydrous aripiprazole Type I). Aripiprazole has the following structural formula (A):

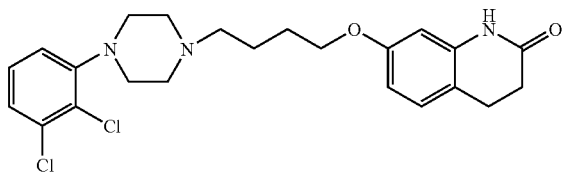

BACKGROUND OF THE INVENTION

Aripiprazole is an atypical antipsychotic agent useful for the treatment of schizophrenia. Schizophrenia is a common type of psychosis characterized by delusions, hallucinations and extensive withdrawal from others. Onset of schizophrenia typically occurs between the age of 16 and 25 and affects 1 in 100 individuals worldwide. It is more prevalent than Alzheimer's disease, multiple sclerosis, insulin-dependent diabetes and muscular dystrophy. Early diagnosis and treatment can lead to significantly improved recovery and outcome. Moreover, early therapeutic intervention may avert costly hospitalization.

U.S. Pat. No. 4,734,416 and U.S. Pat. No. 5,006,528, both assigned to Otsuka, describe aripiprazole and processes for its preparation. These patents also disclose various salts of aripiprazole and their preparation. Preparation of conventional anhydrous aripiprazole Type 1 also was disclosed in Fourth Japanese-Korean Symposium on Separation Technology (Oct. 6-8, 1996). According to the Proceedings of the 4th Japanese-Korean Symposium on Separation Technology, aripiprazole anhydride crystals are manufactured by heating, at 80° C., aripiprazole hydrate previously re-crystallized from an aqueous ethanol solution.

WO 03/026659 (corresponding to U.S. Publication 2004/0058935) also teaches a method of preparing a conventional hydrate of aripiprazole hydrate in which crude aripiprazole crystals are dissolved in a hydrous organic solvent, the solution is heated and then cooled. As described, the organic solvent is one which is miscible with water, such as for example an alcohol, acetone, an ether and their mixtures. Ethanol is apparently preferred. The amount of water in the hydrous solvent can be 10-25% by volume of the solvent, or preferably close to 20% by volume.

US Patent Publication 2005/0277650 alleges that the aripiprazole hydrate prepared as per WO 03/026659 does not provide consistent results and that by an altered process conventional aripiprazole hydrate can be prepared with more consistent results.

In particular, US Patent Publication 2005/0277650 describes a process for preparing aripiprazole hydrate in which aripiprazole is dissolved in an aqueous, organic solvent; the solution is heated to a temperature of above about 67° C.; the heated solution is seeded with aripiprazole hydrate crystals at a temperature of above about 67° C.; the so-seeded solution is cooled to a temperature in the range of about 50° C. to about 55° C. and is maintained at that temperature as crystals form; followed by further cooling of the solution to a temperature in the range of about 0° C. to about 10° C. and maintaining such temperature as crystals form; separating the crystals from the cooled solution; and drying the separated crystals at a temperature of about 45° C. to about 50° C. until the water content of the dried crystals is about 3 to about 4.5 percent by weight.

DETAILED DESCRIPTION OF THE INVENTION

Figure 1:
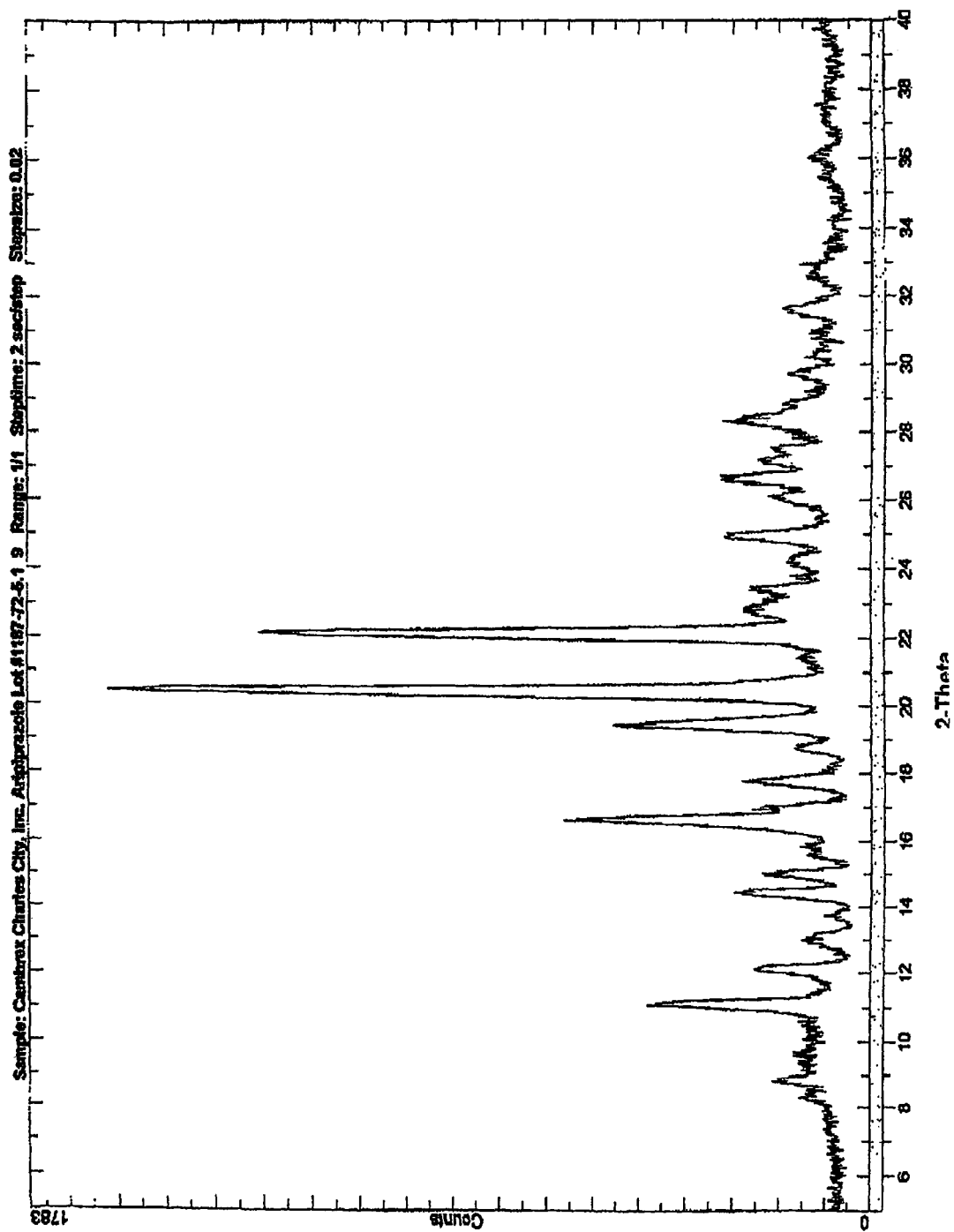
FIG. 1 is an X-ray powder diffractogram (XRD) of the anhydrous aripiprazole crystal obtained on the final sample of Batch 1 dried for 40 hours in a 60 to 65° C. as described in the Example.
Figure 2:
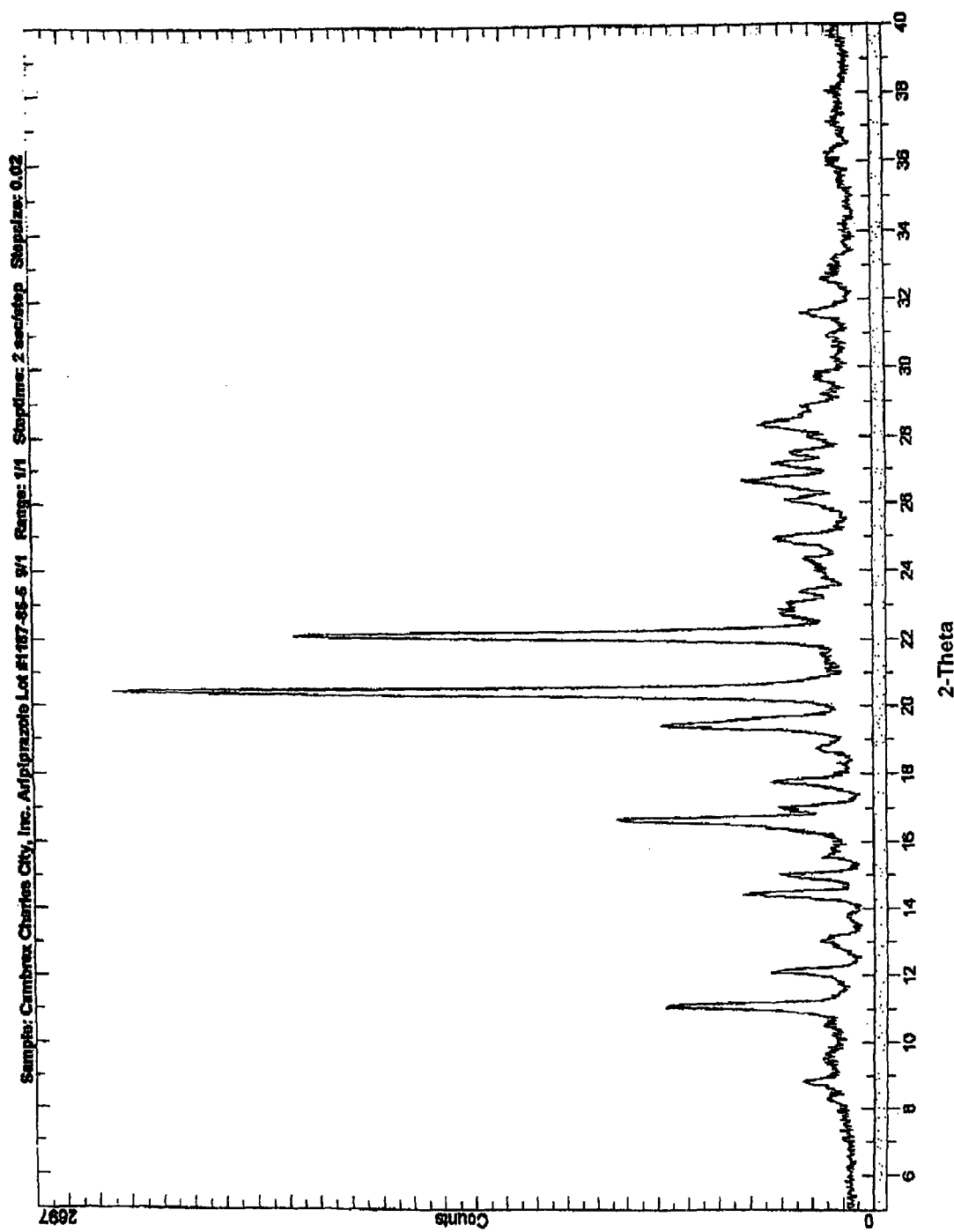
FIG. 2 is an X-ray powder diffractogram (XRD) of the anhydrous aripiprazole crystal obtained on the final sample of Batch 2 dried for 40 hours in a 60 to 65° C. as described in the Example.
Figure 3:
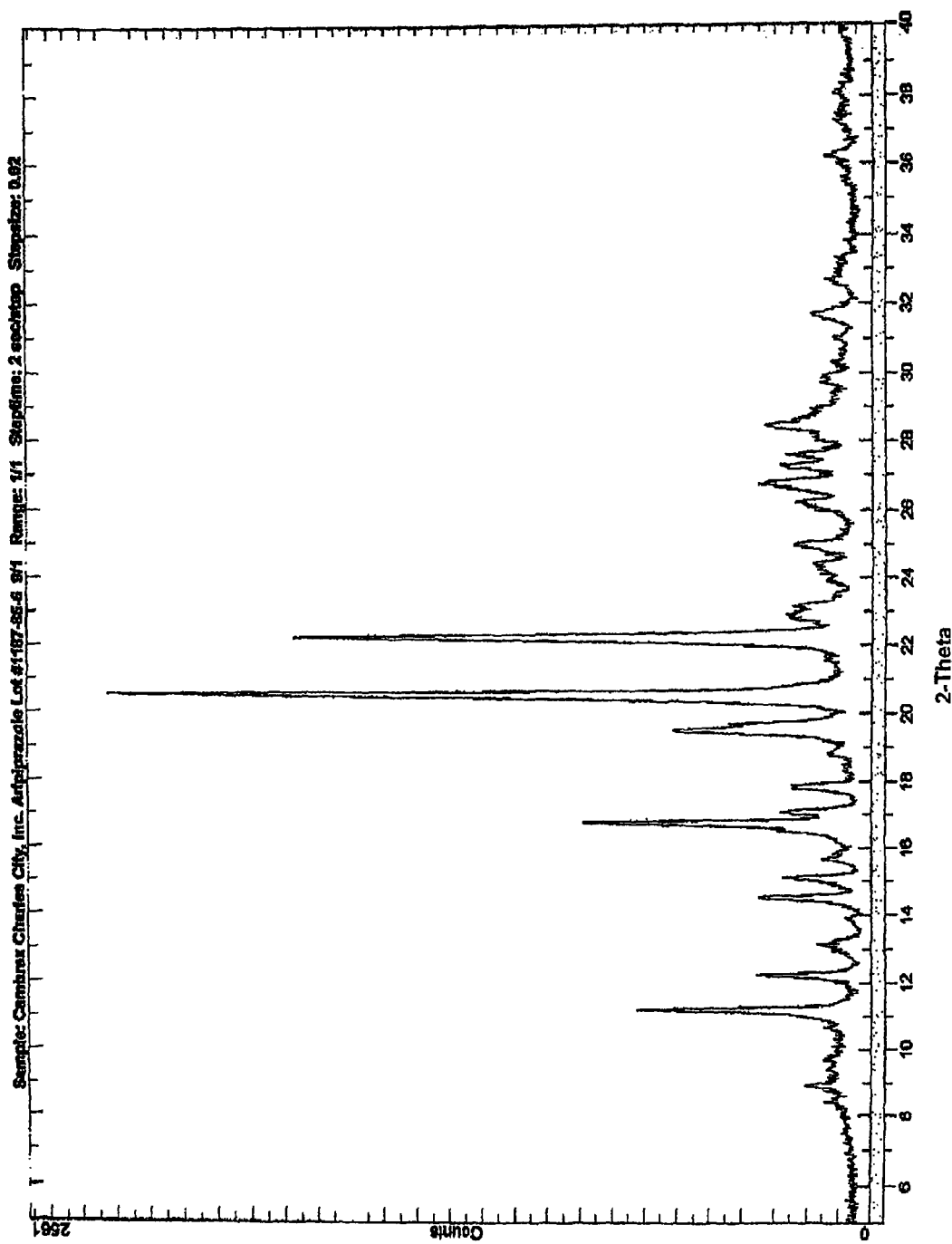
FIG. 3 is an X-ray powder diffractogram (XRD) of the anhydrous aripiprazole crystal obtained on the final sample of Batch 3 dried for 40 hours in a 60 to 65° C. as described in the Example.
Figure 4:
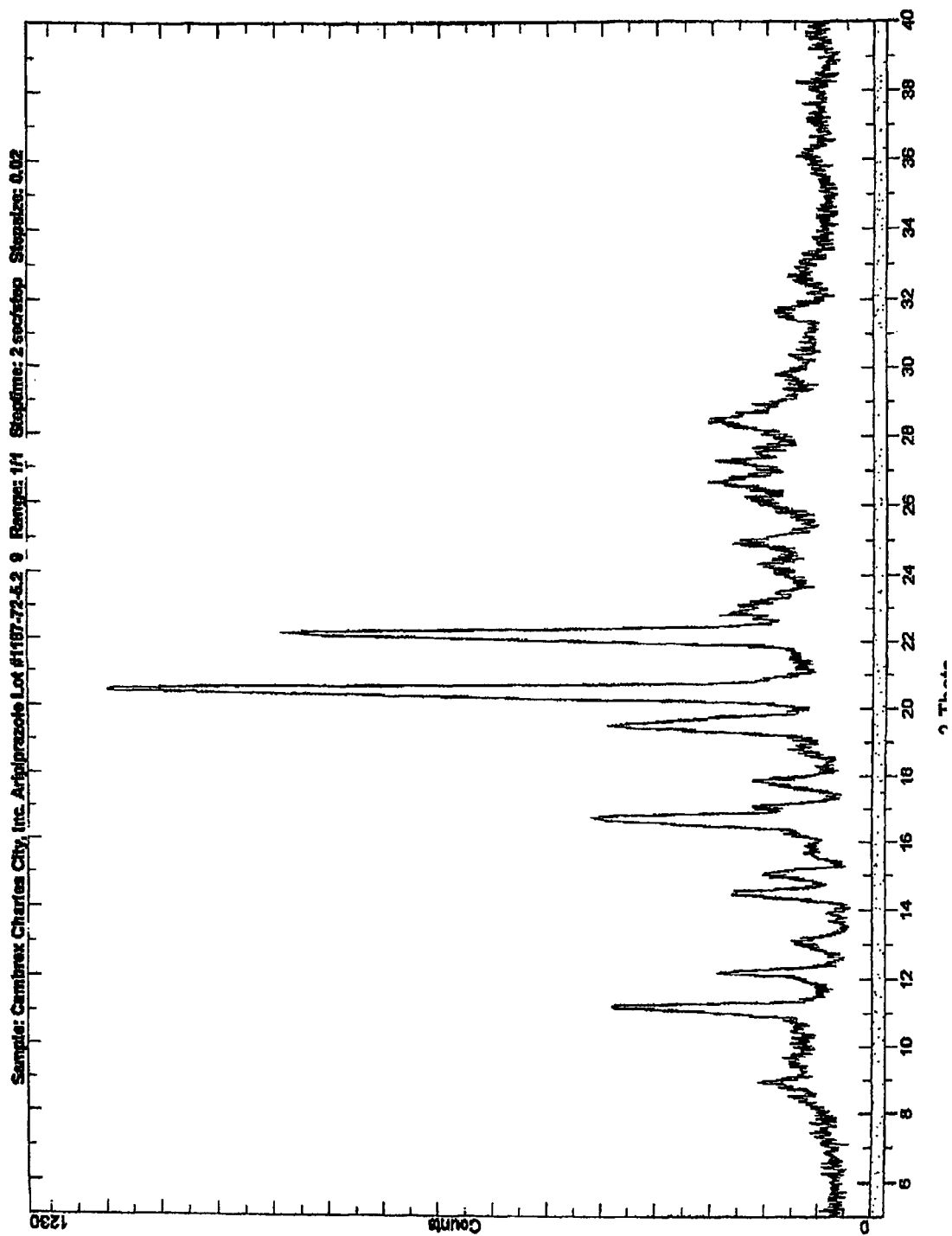
FIG. 4 is an X-ray powder diffractogram (XRD) of the anhydrous aripiprazole crystal obtained on the final sample of Batch 1 dried for 40 hours in a 70 to 80° C. as described in the Example.
Figure 5:
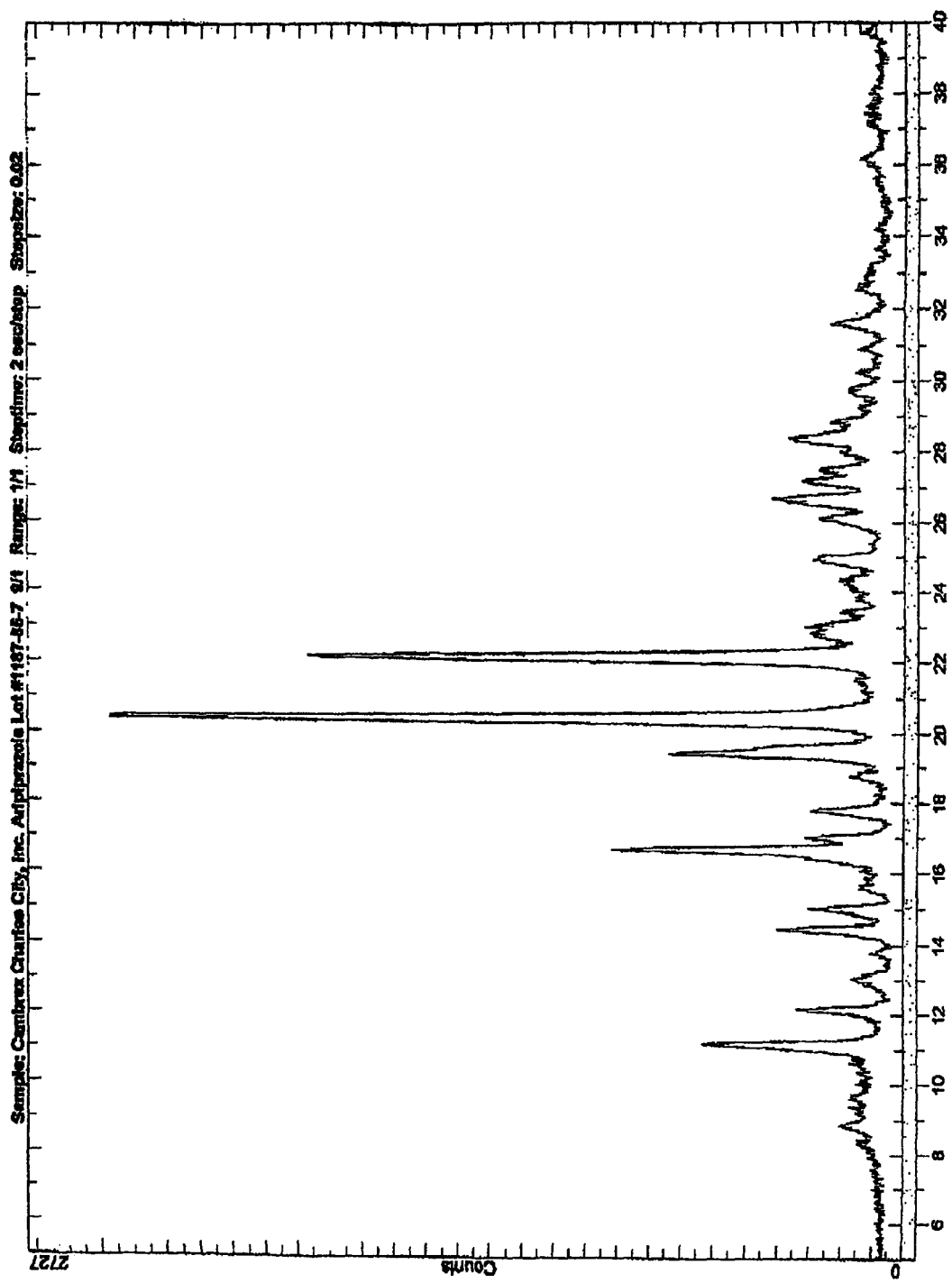
FIG. 5 is an X-ray powder diffractogram (XRD) of the anhydrous aripiprazole crystal obtained on the final sample of Batch 2 dried for 40 hours in a 70 to 80° C. as described in the Example.
Figure 6:
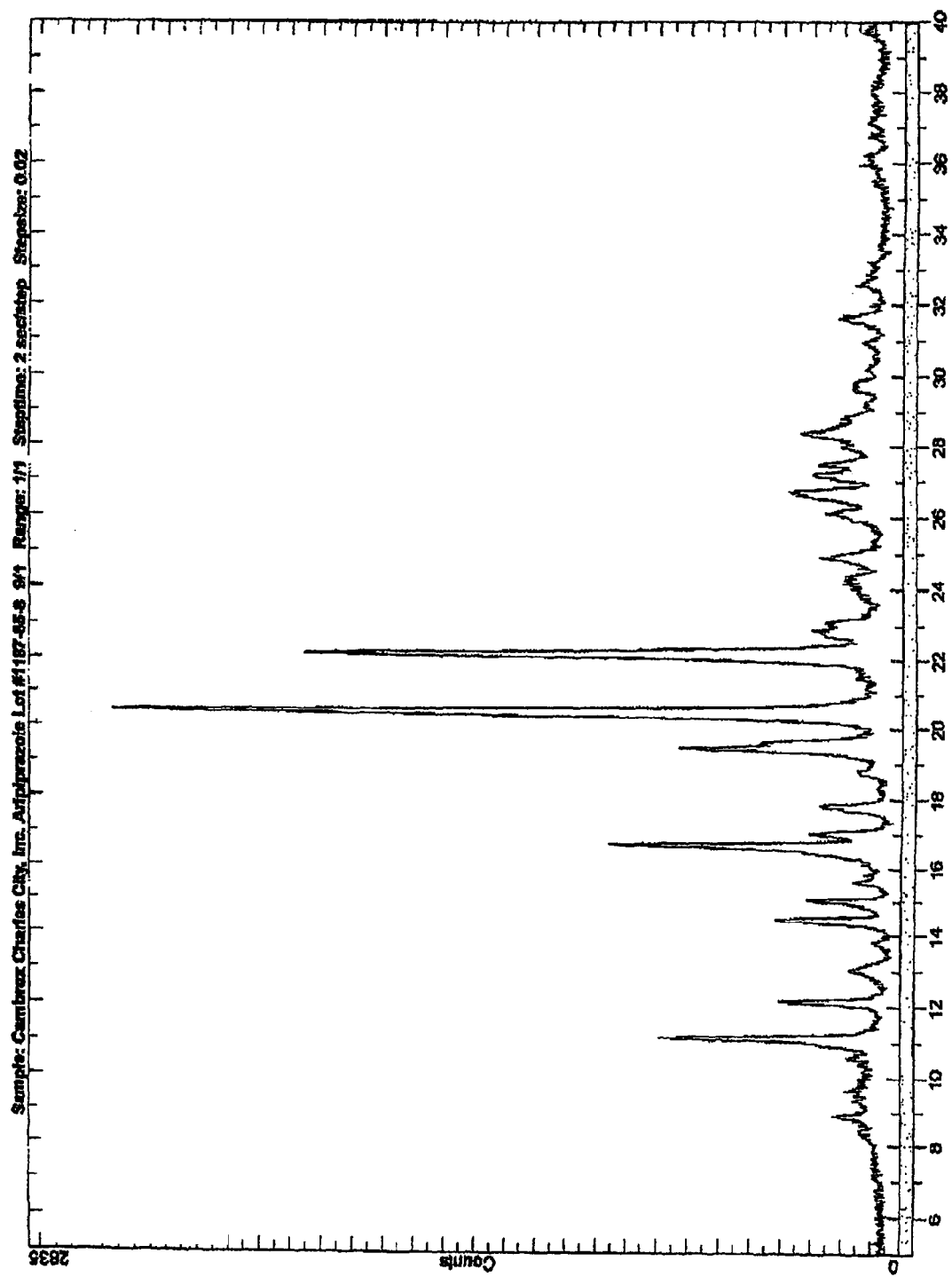
FIG. 6 is an X-ray powder diffractogram (XRD) of the anhydrous aripiprazole crystal obtained on the final sample of Batch 3 dried for 40 hours in a 70 to 80° C. as described in the Example.

The inventors of the present invention have discovered that using conventional, anhydrous Type I crystals to seed an aqueous organic solution of aripiprazole that additional anhydrous Aripiprazole Type I crystals can be obtained in a consistent manner.

Thus, the present invention provides an improved process for the preparation of conventional anhydrous aripiprazole Type I crystals.

In one embodiment, an improved process for the preparation of anhydrous aripiprazole Type I comprises:
(A) dissolving aripiprazole, or an acid salt thereof, in a water miscible organic solvent (preferably an alcoholic solvent), optionally containing up to 50% water (by volume), and usually up to 30% water (by volume), with heating to form a solution of aripiprazole, or an acid salt thereof;
(B) when the solution comprises an acid salt, adding a base to the solution in an amount sufficient to neutralize the acid salt;
(C) optionally contacting the solution with decolorizing carbon or diatomaceous earth;
(D) while maintaining the temperature of the solution above about 70° C., adding sufficient water to produce an aqueous organic solution containing at least 5% water (by volume);
(E) cooling the aqueous organic solution, as required, to a temperature of 25 to 78° C., usually to a temperature of 45 to 78° C., and seeding the solution with anhydrous aripiprazole Type I crystals;
(F) agitating the aqueous organic solution at a temperature in the range of 25 to 78° C., usually at a temperature in the range of 45 to 60° C., to initiate crystallization and form a slurry containing aripiprazole crystals;

(G) cooling the aripiprazole slurry with agitation to a temperature in the range of 15 to 25° C., and maintaining the slurry in that temperature range for at least 2 hours to complete crystal formation;

(H) isolating the crystals by filtration and optionally washing the crystals with organic solvent; and (I) drying the isolated crystals under a vacuum and at a temperature of not greater than 80° C. until the isolated crystals contain less than about 1.0% water by weight.

The water miscible organic solvents that can be used for preparing the anhydrous aripiprazole include alcohols such as methanol, ethanol, isopropanol, n-butanol and pentanol, acetic acid, tetrahydrofuran, acetonitrile and mixtures thereof. Preferably, an alcoholic solvent is used and especially isopropanol (isopropyl alcohol) is used.

The hydrous organic solvent contains from 5 to 50% water by volume, usually 5 to 30% water, more usually 15 to 25% water, and most often about 20% water by volume.

Seeding the aqueous organic solution comprises adding anhydrous aripiprazole Type I crystals, typically in an amount about 0.05% to 1.0% by weight of the dissolved aripiprazole, and usually in an amount of about 0.1% by weight. The seeding crystals are added to the cooled aqueous alcoholic solution at a temperature in the range of 25 to 78° C., usually the cooled aqueous alcoholic solution is at a temperature in the range of 45 to 78° C.

The isolated crystals are preferably dried to a moisture content of less than 0.5%, more usually less that 0.1% and often to a moisture content of less that 0.05%. The isolated crystals are generally dried for a period of time that varies inversely with the temperature. Preferably, the isolated crystals are dried at a temperature in the range of 60 to 70° C., for a period of up to 40 hours. Usually, the drying is accompanied by a vacuum assist.

The process of the present invention constitutes a simple and industrially scaleable process that is pharmaceutically acceptable for the consistent synthesis of anhydrous Type I aripiprazole.

A specific embodiment of the process of the present invention is illustrated in more detail with reference to the following example, which is provided by way of illustration only and should not be construed as a limit on the scope of the appended claims.

EXAMPLE

Preparation of Anhydrous Aripiprazole Type 1

Crude aripiprazole, or an acid salt thereof, can be prepared in any convenient manner. In this example, the source of the aripiprazole is a wet, crude aripiprazole HCl salt.

The aripiprazole HCl (794.5 parts by weight (ppw)), is refluxed in isopropanol (1089.9 ppw) to remove, by distillation, any residual synthesis solvents, and then cooled to terminate reflux conditions. Sodium hydroxide (22.1 ppw of a 50% by weight aqueous solution) is added and stirred for 30 minutes at a temperature of 75-80° C. to neutralize the HCl salt. The pH of a 2 ml sample of the resulting slurry in 10 ml of water should measure not less than 12 (add additional sodium hydroxide as needed to raise the pH to not less than 12). The hot solution then is filtered in contact with either decolorizing carbon or a diatomaceous earth (13 ppw) as an absorbent. The solids, salts and absorbent, are discarded. Keeping the filtrate at a temperature above 70° C., such as between 75-80° C., water is added in an amount (140 ppw) sufficient to provide an aqueous solution of isopropanol containing about 20% by volume water. Then, the solution is cooled to about 60° C. and anhydrous aripiprazole Type I crystals (0.07 ppw) are added and the solution is agitated. Crystallization is initiated by agitating the seeded solution at a temperature in the range of 55-60° C. for one (1) hour and then at a temperature in the range of 45-50° C. for one (1) additional hour. Over a two (2) hour period thereafter, the slurry is gradually cooled to a temperature in the range of 15-25° C. and then held at a temperature in the range of 15-25° C. with agitation for at least an additional two (2) hours. The slurry is filtered, re-slurried with water (285 pbw), filtered again and washed with isopropanol (78.8 pbw) to produce an aripiprazole wet cake.

One portion of an aripiprazole wet cake (20 g), prepared in accordance with the above-described procedure, was placed in a drying oven, the oven maintained at a temperature between 60 to 65° C., and under a vacuum of 22 inches Hg for a period of 40 hours. A dish of phosphorous pentoxide (dessicant) also was placed in the oven. Periodically, approximately a one (1) gram sample of the aripiprazole wet cake was removed from the oven and analyzed for moisture content by the volumetric Karl Fischer titration method and also for its hygroscopicity. At the end of the 40 hour period, the moisture content of the final sample was analyzed using the coulometric Karl Fischer titration method and the hygroscopicity of the sample also was determined. The final moisture content and hygroscopicity values are reported in the Table below.

Another portion of the aripiprazole wet cake (20 g), prepared in accordance with the above-described procedure, was placed in a drying oven, the oven maintained at a temperature between 70 to 80° C., and under a vacuum of 22 inches Hg for a period of 40 hours. A dish of phosphorous pentoxide (dessicant) also was placed in the oven to facilitate drying. Periodically, approximately a one (1) gram sample of the aripiprazole wet cake was removed from the oven and analyzed for moisture content by the volumetric Karl Fischer titration method and also for its hygroscopicity. At the end of the 40 hours, the moisture content of the final sample was analyzed using the coulometric Karl Fischer titration method and the hygroscopicity of the sample also was determined. The final moisture content and hygroscopicity values are reported in the Table below.

TABLE

| | 40 Hours in 60 to 65° C. Oven | | 40 Hours in 70 to 80° C. Oven | |
|---|---|---|---|---|
| | Moisture (%) | Hygroscopicity (%) | Moisture (%) | Hygroscopicity (%) |
| Batch 1 | 0.03 | 3.2 | 0.03 | 0.8 |
| Batch 2 | 0.03 | 1.2 | 0.02 | 0.7 |
| Batch 3 | 0.03 | 1.8 | 0.02 | 0.4 |

As shown, the samples have the hygroscopicity of Type I anhydrous aripiprazole.

XRD data for the anhydrous aripiprazole Batches 1, 2 and 3 produced at the two drying conditions are provided in FIGS. 1 through 6.

The present invention has been described with reference to specific embodiments. However, this application is intended to cover those changes and substitutions that may be made by those skilled in the art without departing from the spirit and the scope of the invention. Unless otherwise specifically indicated, all percentages are by weight. Throughout the specification and in the claims the term "about" is intended to encompass + or −5% and preferably is only about + or −2%.

I claim:

1. A process for preparing hygroscopic anhydrous aripiprazole having major peaks in an X-ray powder diffractogram substantially as shown in FIG. 1 comprising:
   (A) dissolving aripiprazole, or an acid salt thereof, in a water miscible organic solvent, optionally containing up to 50% water (by volume), with heating to form a solution of aripiprazole, or a solution of an acid salt thereof;
   (B) when the solution comprises a solution of an acid salt, adding a base to the solution in an amount sufficient to neutralize the acid salt;
   (C) optionally contacting the solution with decolorizing carbon or diatomaceous earth;
   (D) maintaining the temperature of the solution above about 70° C., and adding sufficient water to produce an aqueous organic solution containing at least 5% water (by volume);
   (E) cooling the aqueous organic solution, as required, to a temperature of 25 to 78° C. and seeding the solution with hygroscopic anhydrous aripiprazole crystals having major peaks in an X-ray powder diffractogram substantially as shown in FIG. 1;
   (F) agitating the aqueous organic solution at a temperature in the range of 25 to 78° C. to initiate crystallization and form a slurry containing aripiprazole crystals;
   (G) cooling the aripiprazole slurry with agitation to a temperature in the range of 15 to 25° C., and maintaining the slurry in that temperature range for at least 2 hours to complete crystal formation;
   (H) isolating the crystals by filtration and optionally washing the crystals with organic solvent; and
   (I) drying the isolated crystals under a vacuum and at a temperature of not greater than 80° C. until the isolated crystals contain less than about 1.0% water by weight.

2. The process according to claim 1, wherein the water miscible organic solvent optionally contains up to 30% water (by volume), the aqueous organic solution is cooled, as required, to a temperature of 45 to 78° C. in step (E) and the aqueous organic solution is agitated at a temperature in the range of 45 to 60° C. in step (F).

3. The process according to claim 2, wherein the organic solvent comprises an alcoholic solvent selected from the group consisting of methanol, ethanol, isopropanol, n-butanol and pentanol.

4. The process according to claim 3, wherein the alcoholic solvent comprises isopropanol.

5. The process according to claim 2, wherein the aqueous organic solution contains about 5 to about 30 percent water (by volume).

6. The process according to claim 5, wherein the aqueous organic solution contains about 15 to about 25 percent water (by volume).

7. The process according to claim 2, wherein seeding is carried out at a temperature in the range of about 45 to 60° C.

8. The process according to claim 7, wherein seeding comprises adding hygroscopic anhydrous aripiprazole crystals having major peaks in an X-ray powder diffractogram substantially as shown in FIG. 1 in an amount of about 0.05 to about 1.0 percent by weight of the original aripiprazole.

9. The process according to claim 8, wherein seeding comprises adding the hygroscopic anhydrous aripiprazole crystals in an amount of about 0.1% by weight of the original aripiprazole.

* * * * *